(12) United States Patent
Guo

(10) Patent No.: US 11,277,899 B2
(45) Date of Patent: *Mar. 15, 2022

(54) SYSTEMS AND METHODS FOR DETERMINING A POSITION OF A FOCAL SPOT OF AN X-RAY SOURCE

(71) Applicant: SHANGHAI UNITED IMAGING HEALTHCARE CO., LTD., Shanghai (CN)

(72) Inventor: Songchao Guo, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/994,762

(22) Filed: Aug. 17, 2020

(65) Prior Publication Data

US 2020/0383195 A1 Dec. 3, 2020

Related U.S. Application Data

(63) Continuation of application No. 16/665,146, filed on Oct. 28, 2019, now Pat. No. 10,750,603, which is a (Continued)

(30) Foreign Application Priority Data

May 31, 2017 (CN) .......................... 201710398128.1

(51) Int. Cl.
*H05G 1/26* (2006.01)
*H05G 1/02* (2006.01)
*A61B 6/00* (2006.01)
*G01T 1/00* (2006.01)
*G01T 1/29* (2006.01)
(Continued)

(52) U.S. Cl.
CPC ............. *H05G 1/26* (2013.01); *A61B 6/4021* (2013.01); *A61B 6/5258* (2013.01); *A61B 6/547* (2013.01); *G01T 1/00* (2013.01); *G01T 1/29* (2013.01); *H05G 1/02* (2013.01); *A61B 6/032* (2013.01); *G21K 1/10* (2013.01)

(58) Field of Classification Search
CPC ..... A61B 6/032; A61B 6/4021; A61B 6/5258; A61B 6/547; G01T 1/00; G01T 1/29; G21K 1/10; H05G 1/02; H05G 1/26
See application file for complete search history.

(56) References Cited

U.S. PATENT DOCUMENTS 5,469,429 A 11/1995 Yamazaki et al.
6,310,938 B1 10/2001 Toth et al.
(Continued)

*Primary Examiner* — Mark R Gaworecki
(74) *Attorney, Agent, or Firm* — Metis IP LLC

(57) ABSTRACT

A system and method for determining a position of a focal spot of an X-ray source may be provided. The system may include a shelter to attenuate X-rays emitted from the focal spot of the X-ray source and an X-ray receiver to receive X-rays. The X-ray receiver may include a plurality of X-ray receiving regions. At least one of the plurality of X-ray receiving regions may X-rays that include attenuated X-rays by the shelter and unattenuated X-rays. The shelter and the X-ray receiver may reside between the X-ray source and an X-ray detector for determining the position of the focal spot.

20 Claims, 8 Drawing Sheets

Related U.S. Application Data continuation of application No. 15/693,328, filed on Aug. 31, 2017, now Pat. No. 10,462,888.

(51) Int. Cl.
*G21K 1/10* (2006.01)
*A61B 6/03* (2006.01)

(56) References Cited

U.S. PATENT DOCUMENTS

| | | |
|---|---|---|
| 6,370,218 B1 | 4/2002 | Toth et al. |
| 10,462,888 B2 * | 10/2019 | Guo ................. A61B 6/547 |
| 2005/0094762 A1 | 5/2005 | Dunham et al. |
| 2005/0129175 A1 | 6/2005 | Shen et al. |
| 2010/0119039 A1 | 5/2010 | Miller et al. |
| 2011/0176663 A1 | 7/2011 | Shaughnessy |
| 2012/0012742 A1 | 1/2012 | Ren et al. |
| 2012/0195404 A1 | 8/2012 | Omura |
| 2013/0077748 A1 | 3/2013 | Althoff |
| 2013/0308748 A1 | 11/2013 | Ikhlef et al. |
| 2014/0042333 A1 | 2/2014 | Niederlohner et al. |
| 2015/0049857 A1 | 2/2015 | Wiedmann |
| 2016/0199019 A1 | 7/2016 | Ruimi et al. |
| 2017/0209106 A1 | 7/2017 | Ikhlef |

* cited by examiner

SYSTEMS AND METHODS FOR DETERMINING A POSITION OF A FOCAL SPOT OF AN X-RAY SOURCE

CROSS-REFERENCE TO RELATED APPLICATIONS

This application is a continuation of U.S. patent application Ser. No. 16/665,146, filed on Oct. 28, 2019, which is a continuation of U.S. patent application Ser. No. 15/693,328 (now U.S. Pat. No. 10,462,888), filed on Aug. 31, 2017, which claims priority of Chinese Patent Application No. 201710398128.1 filed on May 31, 2017, the entire contents of which are hereby incorporated by reference.

TECHNICAL FIELD

The present disclosure generally relates to systems and methods for X-ray imaging, and more particularly, to systems and methods for determining a position of a focal spot of an X-ray source.

BACKGROUND

In an X-ray imaging system, X-rays that are generated by a focal spot of an X-ray source may be used to scan an object. A detector may be situated to face the X-ray source to detect X-rays that strike it. In response to the detected X-rays, the detector may generate signals that are used to reconstruct an image of the object.

During the scanning, it is desired to keep the relative position of the focal spot of the X-ray source to the detector (may be referred to as "relative position" in the following description) unchanged. However, the relative position may change with the working condition of the X-ray source. For example, when the temperature of the X-ray source changes, the relative position may change accordingly. Thereby, it is necessary to develop a system and method for determining the position of the focal spot of the X-ray source during the scanning, and correct the relative position (if necessary) for a subsequent processing (e.g., image reconstruction).

SUMMARY

In accordance with some embodiments of the disclosed subject matter, a system and method for determining a position of a focal spot of an X-ray source are provided.

According to an aspect of the present disclosure, a system for determining a position of a focal spot of an X-ray source is provided. The system may include a shelter that is configured to attenuate X-rays emitted from the focal spot of the X-ray source. The system may further include an X-ray receiver that is configured to receive X-rays. The X-ray receiver may include a plurality of X-ray receiving regions. At least one of the plurality of X-ray receiving regions may receive X-rays that include attenuated X-rays by the shelter and unattenuated X-rays. The shelter and the X-ray receiver may be separated by a distance. The shelter and the X-ray receiver may reside between the X-ray source and an X-ray detector for determining the position of the focal spot.

In some embodiments, the system may include a storage device storing a set of instructions, and at least one processor in communication with the storage device. When executing the instructions, the at least one processor may be configured to cause the system to determine an intensity of the X-rays that strike the at least one of the plurality of X-ray receiving regions. The X-rays that strike the at least one of the plurality of X-ray receiving regions may include attenuated X-rays by the shelter and unattenuated X-rays. The at least one processor may further cause the system to determine, based on the determined intensity of the X-rays that strike the at least one of the plurality of X-ray receiving regions, the position of the focal spot of the X-ray source.

In some embodiments, the plurality of X-ray receiving regions may include two X-ray receiving regions arranged in a first direction and two X-ray receiving regions arranged in a second direction. The first direction may be perpendicular to the second direction.

In some embodiments, one of the two X-ray receiving regions arranged in the first direction may be partially overlapped with one of the two X-ray receiving regions arranged in the second direction.

In some embodiments, the size of one of the two X-ray receiving regions arranged in the first direction may be the same as the size of one of the two X-ray receiving regions arranged in the second direction.

In some embodiments, to determine the intensity of the X-rays that strike the at least one of the plurality of X-ray receiving regions may include to determine a first intensity of the X-rays that strike each of the two X-ray receiving regions arranged in the first direction, and to determine a second intensity of the X-rays that strike each of the two X-ray receiving regions arranged in the second direction.

In some embodiments, to determine, based on the determined intensity of the X-rays that strike the at least one of the plurality of X-ray receiving regions, the position of the focal spot of the X-ray source may include to determine, based on the first intensities, the position of the focal spot in the first direction, determine, based on the second intensities, the position of the focal spot in the second direction, and determine, based on the position of the focal spot in the first direction and the position of the focal spot in the second direction, the position of the focal spot.

In some embodiments, to determine the position of the focal spot in the first direction may include to determine the position of the focal spot in the first direction based on a relationship between positions of the focal spot and distributions of intensities of the X-rays that strike the at least one of the plurality of X-ray receiving regions.

In some embodiments, to determine the position of the focal spot in the first direction may include to determine the position of the focal spot in the first direction based on a difference between the intensities of the X-rays that strike at least two of the plurality of X-ray receiving regions.

In some embodiments, to determine the position of the focal spot in the first direction may include to determine the position of the focal spot in the first direction based on a ratio between the intensities of the X-rays that strike at least two of the plurality of X-ray receiving regions.

In some embodiments, the shelter may have a shape of a cross, a rectangle, a circle, or a triangle.

In some embodiments, at least a portion of the at least one of the plurality of X-ray receiving regions may receive the unattenuated X-rays emitted from the focal spot of the X-ray source.

According to an aspect of the present disclosure, a method for determining a position of a focal spot of an X-ray source is provided. The method may be implemented on at least one machine, each of which has at least one processor and storage. The method may include attenuating, by a shelter, X-rays emitted from the focal spot of the X-ray source, and receiving, by an X-ray receiver, X-rays that include the attenuated X-rays by the shelter and unattenuated X-rays. The X-ray receiver may have a plurality of X-ray receiving regions. The method may further include determining, by at least a processor, an intensity of the X-rays that strike at least one of the plurality of X-ray receiving regions, and determining, based on the determined intensity of the X-rays that strike the at least one of the plurality of X-ray receiving regions, the position of the focal spot of the X-ray source.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
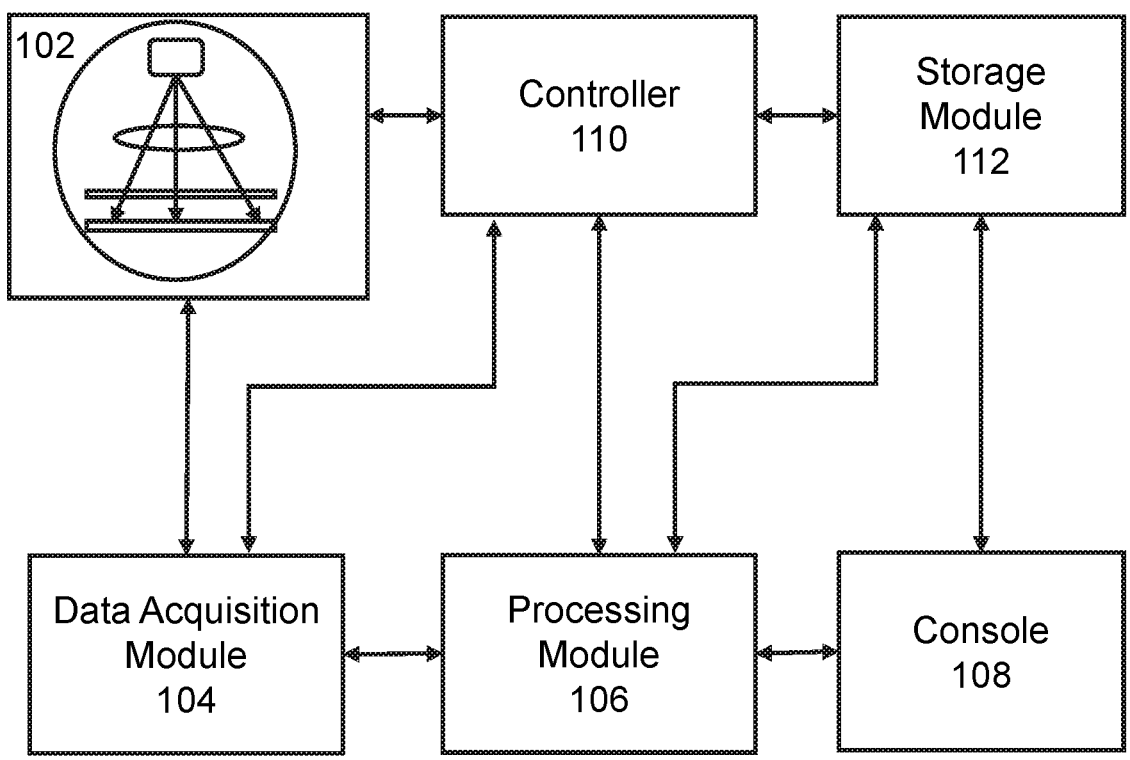
FIG. 1 is a schematic block diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is to describe particular exemplary embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding the present disclosure. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

To avoid deficiencies that may be caused by the variation of a focal spot of an X-ray source, implementations of the present disclosure provide for mechanisms (which may include methods, systems, computer-readable medium, etc.) for determining the position of the focal spot of the X-ray source. For example, the mechanisms may determine the position of the focal spot of the X-ray source based on a shelter and an X-ray receiver that has a plurality of X-ray receiving regions. The shelter may have a properly designed shape or configuration, and attenuate X-rays that strike it. With the shelter situated between the X-ray source and the X-ray receiver, the densities of X-rays that strike different X-ray receiving regions of the X-ray receiver may vary with the position of the focal spot of the X-ray source. Thereby, the position of the focal spot of the X-ray source may be determined according to the densities of X-rays that strike different regions of the X-ray receiver.

FIG. 1 is a schematic block diagram of an exemplary imaging system 100 according to some embodiments of the present disclosure. As shown, the imaging system 100 may include an imaging apparatus 102, a data acquisition module 104, a processing module 106, a console 108, a controller 110, and a storage module 112. It should be noted that the imaging system described below is merely provided for illustration purposes, and not intended to limit the scope of the present disclosure. The imaging system 100 may find its applications in various fields, for example, healthcare industries (e.g., medical applications), security applications, industrial applications, etc. For example, the imaging system 100 may be used for internal inspections of components including, e.g., flaw detection, security scanning, failure analysis, metrology, assembly analysis, void analysis, wall thickness analysis, or the like, or a combination thereof. The imaging system may be a computed tomography (CT) system, a digital radiography (DR) system, a computed radiography (CR) scanner, a multi-modality system, or the like, or a combination thereof.

Generally, the terms "module," "unit," and/or "engine" used herein, refers to logic embodied in hardware or firmware, or to a collection of software instructions. The modules, units, and engines described herein may be implemented as software and/or hardware modules and may be stored in any type of non-transitory computer-readable medium or another storage device. In some embodiments, a software module may be compiled and linked into an executable program. It will be appreciated that software modules can be callable from other modules or themselves, and/or can be invoked in response to detected events or interrupts. Software modules configured for execution on computing devices (e.g., processor 220 or CPU 340) can be provided on a computer readable medium, such as a compact disc, a digital video disc, a flash drive, a magnetic disc, or any other tangible medium, or as a digital download (and can be originally stored in a compressed or installable format that requires installation, decompression, or decryption prior to execution). Such software code can be stored, partially or fully, on a memory device of the executing computing device, for execution by the computing device. Software instructions can be embedded in firmware, such as an EPROM. It will be further appreciated that hardware modules can be included of connected logic units, such as gates and flip-flops, and/or can be included of programmable units, such as programmable gate arrays or processors. The modules or computing device functionality described herein are preferably implemented as software modules but can be represented in hardware or firmware. In general, the modules described herein refer to logical modules that can be combined with other modules or divided into sub-modules despite their physical organization or storage.

The imaging apparatus 102 may be a computed tomography (CT) scanner, a digital radiography (DR) scanner, a computed radiography (CR) scanner, a multimodality imaging device, or the like, or a combination thereof. Exemplary multi-modality imaging devices may include a computed tomography-positron emission tomography (CT-PET) scanner, a computed tomography-magnetic resonance imaging (CT-MRI) scanner, etc. The imaging apparatus 102 may generate a signal by scanning an object with radiation beams. The radiation beams may include X-rays. The object may include a substance, tissue, an organ, a specimen, a body, a human being, or the like, or a combination thereof. The signal may contain characteristic information of the object (e.g., density, thickness, composition). In some embodiments, a detector in the imaging apparatus 102 may detect a radiation beam traversing an object to generate a signal. For example, the detected radiation beam may excite a scintillating material on the detector to generate an optical signal. In some embodiments, the imaging apparatus 102 may include one or more devices that are configured to collect data relating to the working condition of one or more components of the imaging apparatus 102. For example, the one or more devices may collect data relating to the position of a focal spot of an X-ray source in the imaging apparatus 102. The data relating to the working condition of one or more components of the imaging apparatus 102 may be transmitted to, for example, the processing module 106 for subsequent processing.

The data acquisition module 104 may obtain a signal generated by the imaging apparatus 102. For example, the data acquisition module 104 may receive an optical signal from a detector of the imaging apparatus 102. The data acquisition module 104 may include an optoelectronic conversion unit, an analog-digital converter (ADC), or the like, or a combination thereof. The optoelectronic conversion unit may convert the optical signal into an electronic signal. The analog-digital converter may further convert the electronic signal into a digital signal, such as a digital signal that encodes projection data of an object. The projection data may be transmitted to other components (e.g., the processing module 106) in the imaging system 100 for further processing. It should be noted that, in some embodiments, the optoelectronic conversion unit and/or the analog-digital converter may be unnecessary, or may be integrated into the imaging apparatus 102.

The processing module 106 may generate an image based on data relating to an object obtained from other components in the imaging system 100, for example, the data acquisition module 104, or the storage module 112. The image may be generated using a suitable analytical reconstruction technique, an iterative reconstruction technique, and/or other reconstruction techniques. Alternatively or additionally, the processing module 106 may determine a working condition of the imaging apparatus 102 (e.g., the position of one or more components of the imaging apparatus 102), and generate an image based on the working condition of the imaging apparatus. The processing module 106 may be connected to or communicate with the data acquisition 104, the console 108, the controller 110, and the storage 112 via a wireless connection, a wired connection, or a combination thereof.

The console 108 may be a user interface through which a user or an operator may communicate with different components in the imaging system 100. The console 108 may include an input device, a control panel, etc. The input device may include alphanumeric and other keys that may be input via, for example, a keyboard, a touch screen (e.g., with a haptics or tactile feedback), a speech input, an eye tracking input, a brain monitoring system, or any other comparable input mechanism. The input device may also include, for example, a cursor control device, such as a mouse, a trackball, or cursor direction keys, etc. In some embodiments, the console 108 may display images generated by the processing module 106. The console 108 may send a command or an instruction from a user or an operator to the processing module 106, and/or the controller 110. The console 108 may set one or more parameters for the imaging system 100, including acquisition parameters and/or reconstruction parameters. The acquisition parameters may relate to one or more conditions in obtaining scan data by, for example, scanning an object. The reconstruction parameters may relate to one or more conditions in reconstructing an image of an object. For example, the acquisition parameters may include a tube voltage, a tube current, recon parameters (e.g., a slice thickness), a scan time, a collimation/slice width, a beam filtration, a helical pitch, etc. The reconstruction parameters may include a reconstruction field of view (FOV), a reconstruction matrix, a convolution kernel/reconstruction filter, etc.

The controller 110 may control the imaging apparatus 102, the data acquisition module 104, the processing module 106, the console 108, and/or the storage module 112. For example, the controller 110 may control the imaging apparatus 102 to rotate to a desired position that may be prescribed by a user via the console 108. The controller 110 may control the parameters of radiation beams, including the intensity of radiation beams. As another example, the controller 110 may control the display of images on the console 108. In some embodiments, the controller 110 may control the data acquisition module 104 to acquire a signal generated from the imaging apparatus 102. Furthermore, the controller 110 may control the processing module 106 to generate an image based on data received from the data acquisition module 104.

The controller 110 may include a processor, a processing core, memory, or the like, or a combination thereof. Specifically, the controller 110 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a microcontroller unit, a microprocessor, an advanced RISC machines processor (ARM), or the like, or a combination thereof.

The storage module 112 may store data relating to the imaging system 100. The data may be a numerical value, an image, information of a subject, an instruction and/or a signal to operate the imaging apparatus 102, voice, a model relating to a patient, an algorithm relating to an image processing technique, or the like, or a combination thereof. Exemplary numerical values may include a threshold, a CT value, a value relating to an anti-scatter grid, or the like, or a combination thereof. Exemplary images may include a raw image or a processed image (e.g., an image after pretreatment). Exemplary models relating to a patient may include the background information of the patient, for example, ethnicity, citizenship, religion, gender, age, matrimony state, height, weight, medical history (e.g., history relating to different organs, or tissues), job, personal habits, or the like, or a combination thereof.

The storage module 112 may include a random-access memory (RAM), a read-only memory (ROM), or the like, or a combination thereof. The random-access memory (RAM) may include a dekatron, a dynamic random-access memory (DRAM), a static random-access memory (SRAM), a thyristor random access memory (T-RAM), a zero-capacitor random access memory (Z-RAM), or the like, or a combination thereof. The read only memory (ROM) may include a bubble memory, a magnetic button line memory, a memory thin film, a magnetic plate line memory, a core memory, a magnetic drum memory, a CD-ROM drive, a hard disk, a flash memory, or the like, or a combination thereof. The storage module 112 may be a removable storage device such as a U flash disk that may read data from and/or write data to the processing module 106 in a certain manner. The storage module 112 may also include other similar means for providing computer programs or other instructions to operate the modules/units in the imaging system 100. The storage module 112 may be operationally connected with one or more virtual storage resources (e.g., a cloud storage, a virtual private network, other virtual storage resources, etc.) for transmitting or storing the data into the one or more virtual storage resources.

In some embodiments, the imaging system 100 may be connected to a network (not shown in the figure). The network may be a local area network (LAN), a wide area network (WAN), a public network, a private network, a proprietary network, a public switched telephone network (PSTN), the Internet, a virtual network, a metropolitan area network, a telephone network, or the like, or a combination thereof. The connection between different components in the imaging system 100 may be wired or wireless. The wired connection may include using a metal cable, an optical cable, a hybrid cable, an interface, or the like, or a combination thereof. The wireless connection may include using a wireless local area network (WLAN), a wireless wide area network (WWAN), a Bluetooth, a ZigBee, a near field communication (NFC), or the like, or a combination thereof.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage module 112 may be a database including cloud computing platforms, such as a public cloud, a private cloud, a community and hybrid clouds, etc. As another example, the data acquisition module 104 may be implemented on the imaging apparatus 102. As a further example, the controller 110 and the storage module 112 may be integrated into one module. However, those variations and modifications do not depart the scope of the present disclosure.

Figure 2:
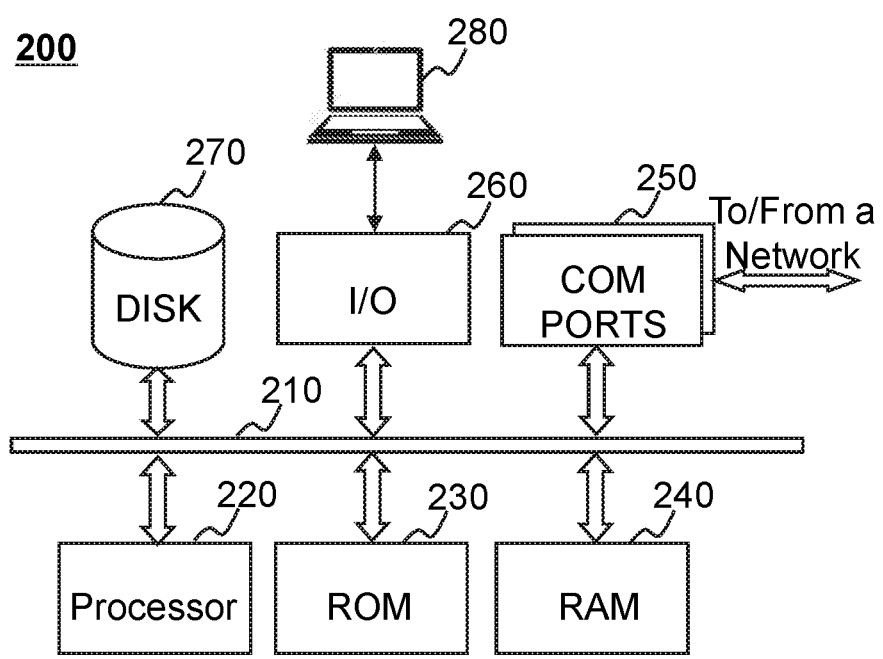
FIG. 2 is a schematic diagram illustrating hardware and/or software components of an exemplary computing device on which a processing engine may be implemented according to some embodiments of the present disclosure.

FIG. 2 is a schematic diagram illustrating exemplary hardware and/or software components of an exemplary computing device 200 on which the processing module 106 may be implemented according to some embodiments of the present disclosure. As illustrated in FIG. 2, the computing device 200 may include an internal communication bus 210, a processor 220, a read-only memory (ROM) 230, a random access memory (RAM) 240, a communication port 250, an input/output (I/O) 260, a disk 270, and a display 280 connected to the I/O 260.

The internal communication bus 210 may be used for data communication. In some embodiments, components of the computing device 200 may communicate data with each other via the internal communication bus 210. For example, the processor 220 may send data to the ROM 230, the RAM 240, or the I/O 260. In some embodiments, the data may include an instruction code, status information and/or control information. In some embodiments, the internal communication bus 210 may include an Industry Standard Architecture (ISA) bus, an Extended Industry Standard Architecture (EISA) bus, a Video Electronic Standard Association (VESA) bus, a peripheral component interconnect (PCI) bus, or the like, or any combination thereof.

The processor 220 may execute computer instructions (e.g., program code) and perform functions of the processing module 106 in accordance with techniques described herein. The computer instructions may include, for example, routines, programs, objects, components, data structures, procedures, modules, and functions, which perform particular functions described herein. For example, the processor 220 may process image data obtained from the imaging apparatus 102, the data acquisition module 104, the processing module 106, and/or any other component of the imaging system 100. In some embodiments, the processor 220 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The ROM 230 may be employed for power on self-test of the processing module 106, initialization of the components of the processing module 106, drive programs of the I/O of the processing module 106. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc.

The RAM 240 may store an operating system, applications, data, etc. The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc.

The communication port 250 may be connected to a network to facilitate data communications. The communication port 250 may establish connections between the processing module 106 and the imaging apparatus 102, the data acquisition module 104, the processing module 106, and/or the storage module 112. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMAX™ link, a WLAN link, a ZigBee link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 250 may be a specially designed communication port. For example, the communication port 250 may be designed in accordance with the digital imaging and communications in medicine (DICOM) protocol.

The I/O 260 may input and/or output signals, data, information, etc. In some embodiments, the I/O 260 may enable a user interaction with the processing module 106. In some embodiments, the I/O 260 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The disk 270 may store data or information generated by the processing module 106. The disk 270 may include a hard disk drive (HDD), a solid-state drive (SSD), a hybrid hard drive (HHD), etc.

The display 280 may present data or information generated by the processing module 106 to a user. In some embodiments, the display 280 may include a physical display including, for example, a display with a loudspeaker, a liquid crystal display (LCD), a light emitting diode (LED) display, an organic light emitting diode (OLED) display, an E-ink display.

Figure 3:
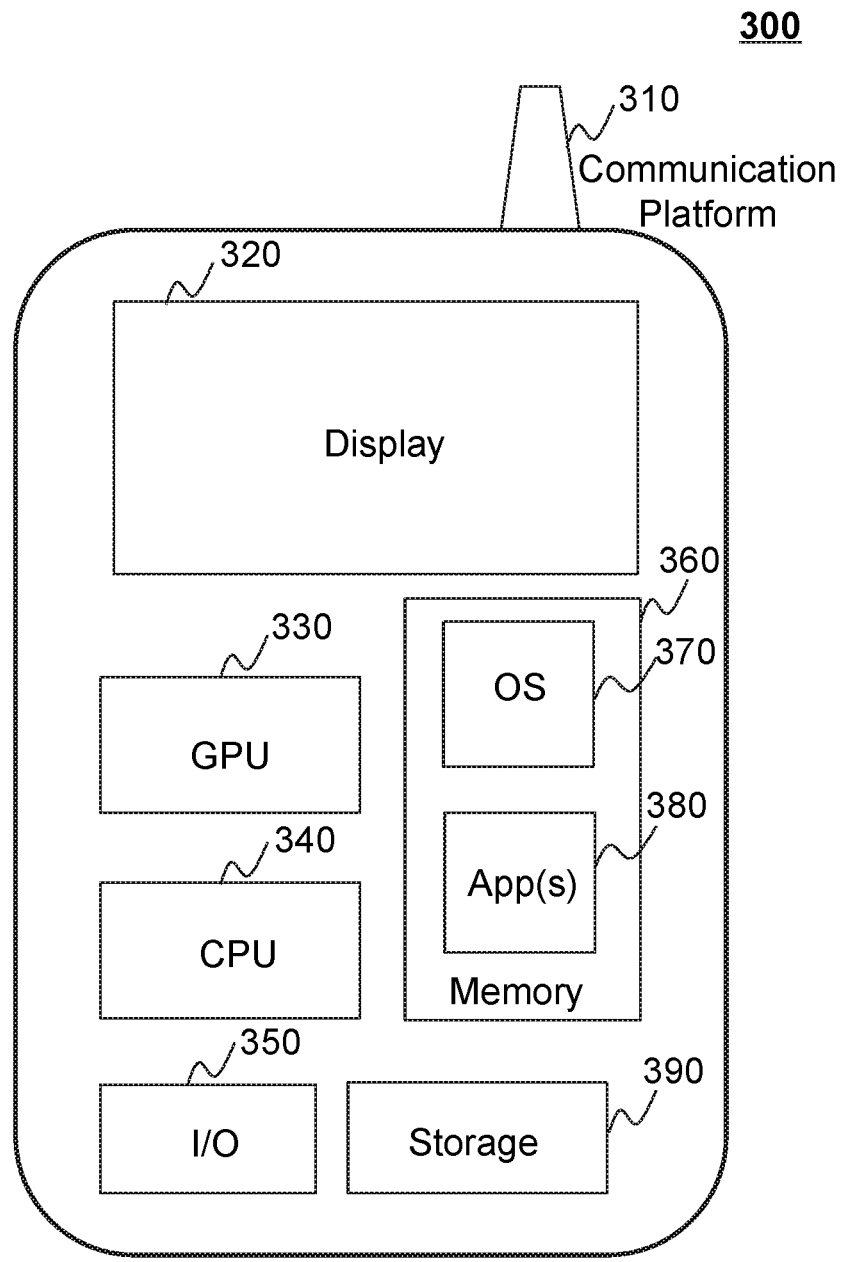
FIG. 3 is a schematic diagram illustrating hardware and/or software components of an exemplary mobile device on which a terminal may be implemented according to some embodiments of the present disclosure.

FIG. 3 is a schematic diagram illustrating exemplary hardware and/or software components of an exemplary mobile device 300 on which the processing module 106 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing module 106. User interactions with the information stream may be achieved via the I/O 350 and provided to the processing module 106 and/or other components of the imaging system 100 via a network.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
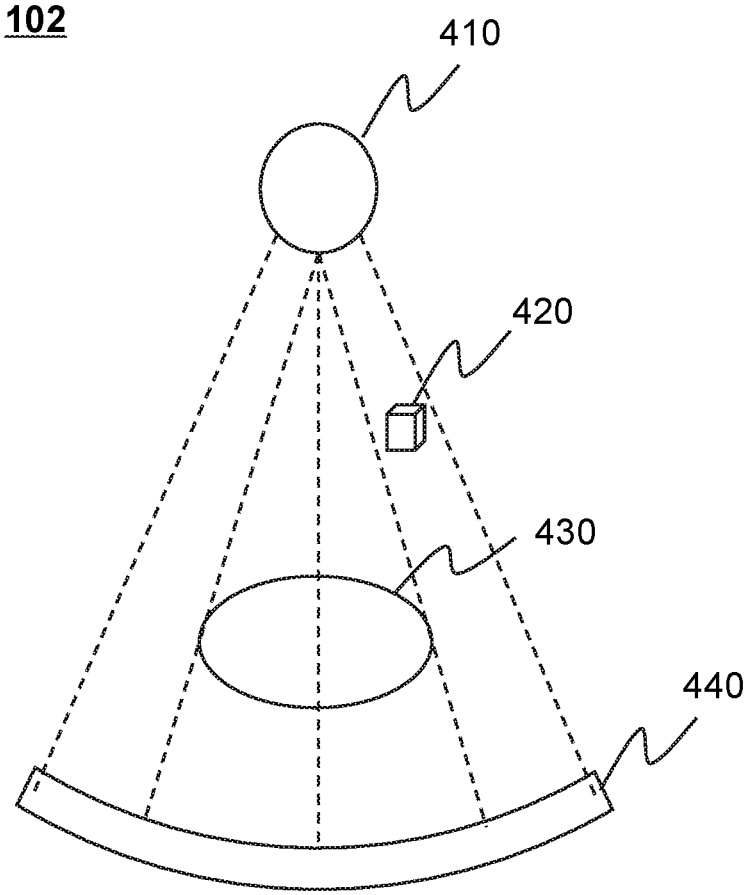
FIG. 4 is a schematic diagram illustrating an exemplary imaging apparatus according to some embodiments of the present disclosure.

FIG. 4 is a schematic diagram illustrating an exemplary imaging apparatus 102 according to some embodiments of the present disclosure. The imaging apparatus 102 may include an X-ray source 410, a tracking device 420 and a detector 440. The tracking device 420 may reside between the X-ray source 410 and the detector 440. During a scanning process, an object 430 may reside between the X-ray source 410 and the detector 440. In some embodiments, the imaging apparatus 102 may be used in an imaging system, for example, a CT system, a CR system, a DR system, a CT-PET system, or a CT-MRI system.

The X-ray source 410 may generate X-rays. The X-ray source 410 may include an X-ray tube that is configured to generate the X-rays under a power supply. For illustration purpose, the X-ray tube may include a cathode and an anode that is situated to face the cathode. When the cathode is powered by the power supply, electrons may be liberated from the cathode and move toward the anode under the effect of an electric field between the cathode and the anode. When the electrons impinge on the anode, X-rays may be generated by a focal spot on the anode. The focal spot may refer to the area on the anode that receives the electrons. The position of the focal spot on the anode may vary with, for example, the power provided by the power supply, the electric field applied between the cathode and the anode, or the ambient temperature of the anode.

The tracking device 420 may determine the position of the focal spot of the X-ray source. The tracking device 420 may include an X-ray receiver that is configured to receive X-rays emitted from the focal spot of the X-ray source. The X-ray receiver may generate an electrical signal in response to X-rays that strike the X-ray receiver. In some embodiments, the electrical signal may be associated with the incident angles of the X-rays that strike the X-ray receiver. In some embodiments, the electrical signal may be associated with the intensity of X-rays that strike the X-ray receiver or a part thereof.

The X-ray receiver may be connected to a component that is capable of processing the electrical signal. In some embodiments, the X-ray receiver may transmit the electrical signal to one or more components in the imaging system 100 (e.g., the processing module 106) to determine the position of the focal spot. For example, the processing module 106 may determine the incident angles of the X-rays that strike the X-ray receiver based on the electrical signal. Then the processing module 106 may determine the position of the focal spot based on the incident angles of the X-rays that strike the X-ray receiver. As another example, the processing module 106 may determine the intensity of the X-rays that strike the X-ray receiver or a part thereof based on the electrical signal. Then the processing module 106 may determine the position of the focal spot based on the intensity of the X-rays that strike the X-ray receiver or a part thereof. In some embodiments, the X-ray receiver may be connected to an external position determination module that is configured to determine the position of the focal spot of the X-ray source based on the electrical signal. As used herein, the position determination module refers to logic embodied in hardware or firmware, or to a collection of software instructions. The position determination module may be implemented as software and/or hardware modules and may be stored in any type of non-transitory computer-readable medium or another storage device. For example, the position determination module may be implemented in the computing device 200 illustrated in FIG. 2 (e.g., the processor 220) or the mobile device 300 illustrated in FIG. 3 (e.g., CPU 340).

The detector 440 may detect the X-rays traversing the object 430. The detector 440 may include a plurality of detection units. In some embodiments, the plurality of detection units may be positioned to form an arcuate structure. The detector 440 may be connected to one or more components of the imaging system 100 (e.g., the data acquisition module 104). For example, the data acquisition module 104 may receive data related to the object 430 from the detector 440, and further transmit the data related to the object 430 to the processing module 106 for image reconstruction.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the tracking device 420 may be a device that is detachable from, for example, the X-ray source 410, or the detector 440. As another example, the tracking device 420 may be located at any position between the X-ray source 410 and the object 430. Alternatively, it shall be understood that the tracking device 430 may also be located behind the object 430 as long as the tracking device 420 has an unobstructed view of the X-ray source 410. As still another example, the imaging apparatus 120 may include a collimator configured to shape the X-rays generated by the focal spot. The tracking device 420 may be located adjacent to the tracking device 420 without affecting the shaped X-rays. However, those variations and modifications do not depart the scope of the present disclosure.

Figure 5:
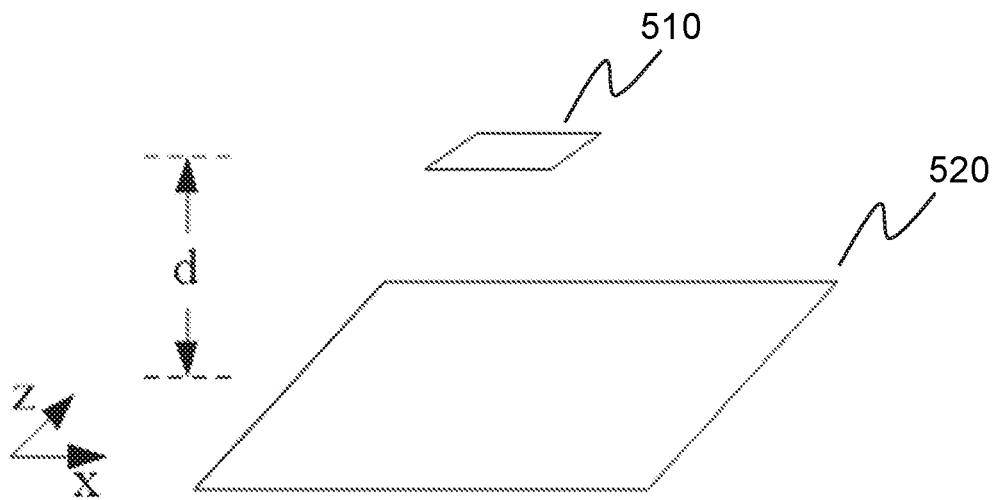
FIG. 5 is a schematic diagram illustrating an exemplary tracking device according to some embodiments of the present disclosure.

FIG. 5 is a schematic diagram illustrating an exemplary tracking device 500 according to some embodiments of the present disclosure. In some embodiments, the tracking device 500 may be used as a component of the imaging apparatus 102 (e.g., the tracking device 420 or a part thereof). The tracking device 500 may include a shelter 510 and an X-ray receiver 520. The X-ray receiver 520 may have a surface that is parallel to the x-z plane as illustrated in FIG. 5. The shelter 510 and the X-ray receiver 520 may be separated by a distance d along the direction that is perpendicular to the x-z plane (e.g., the y direction).

The shelter 510 may attenuate the X-rays that strike it. When X-rays strike the shelter 510, a first portion of the X-rays may be absorbed or scattered by the shelter 510, and a second portion of the X-rays may pass through the shelter 510. In some embodiment, a ratio between the intensity of the second portion of the X-rays and the intensity of the first portion of the X-rays may be less than 80%, or less than 50%, or less than 30%, or less than 10%, or less than 5%, or less than 1%, etc.

Figure 6:
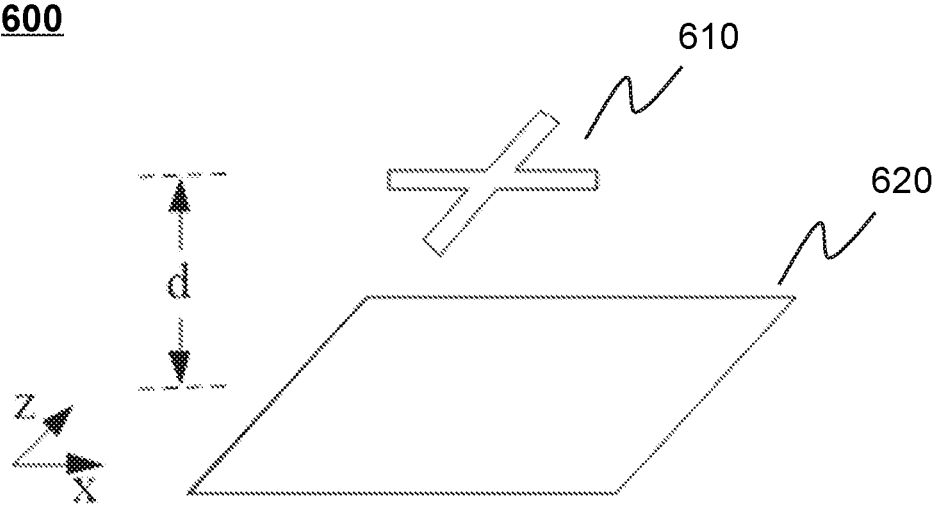
FIG. 6 is a schematic diagram illustrating an exemplary tracking device according to some embodiments of the present disclosure.

The shelter 510 may include materials that are capable of absorbing X-rays (also referred to herein as "highly absorbing materials"). Exemplary highly absorbing materials may include tungsten, lead, uranium, gold, silver, copper, molybdenum, plumbum, or the like, or a combination thereof. Additionally or alternatively, the shelter 510 may include materials that may allow X-rays to pass (also referred to herein as "poorly absorbing materials"). Exemplary poorly absorbing materials may include resin, fiber, rubber, inorganic non-metallic material (e.g., ceramics), etc. As used herein, a highly absorbing material and a poorly absorbing material may absorb different amounts of X-rays. For example, the highly absorbing material may absorb a greater amount of the radiation than the poorly absorbing material. In some embodiments, the shelter 510 may be formed by the highly absorbing material. For example, the highly absorbing material may be made into a properly designed shape or configuration (e.g., the shelter 610 as illustrated in FIG. 6). In some embodiments, the shelter 510 may be partially formed by the highly absorbing material and partially formed by the poorly absorbing material. For example, the poorly absorbing material may be fabricated to fill one or more gaps in a structure that is formed by the highly absorbing material.

The shelter 510 may have various shapes, for example, a cross, a rectangle, a circle, a star, a snowflake, or a triangle. The shape of the shelter 510 may affect the distribution of the X-rays that strike the X-ray receiver 520. More descriptions regarding the distribution of the X-ray that strike the X-ray receiver may be found elsewhere in the present disclosure (e.g., FIG. 10 and the description thereof).

The X-ray receiver 520 may receive X-rays that strike it. The X-rays that strike the X-ray receiver 520 may include unattenuated X-rays that are not attenuated by the shelter 510 and attenuated X-rays that pass through the shelter 510. In some embodiments, the X-ray receiver 520 may include a plurality of X-ray receiving regions. An X-ray receiving region may include one or more detection units that generate an electrical signal in response to the X-rays that strike the X-ray receiving region. In some embodiments, the electrical signal may be associated with the intensity of the X-rays that strike the X-ray receiving region. More description regarding the plurality of the X-ray receiving region may be found elsewhere in the disclosure (e.g., FIG. 7, FIG. 8, and the description thereof).

In some embodiments, the X-ray receiver 520 may be connected to a component of the imaging system 100 that is capable of processing the electrical signal generated by an X-ray receiving region. For example, the X-ray receiver 520 may transmit the electrical signal to the processing module 106 of the imaging system 100 such that the processing module 106 may determine the position of the focal spot of the X-ray source based on the electrical signal. As another example, the X-ray receiver 520 may transmit the electrical signal to a position determination module that is implemented in the computing device 200 illustrated in FIG. 2 (e.g., the processor 220) or the mobile device 300 illustrated in FIG. 3 (e.g., CPU 340). In some embodiments, the position determination module may be integrated as part of the X-ray receiver 520. In some embodiments, the position determination module may be in wired or wireless connection with the X-ray receiver.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the distance d between the shelter 510 and the X-ray receiver 520 may be adjustable. However, those variations and modifications do not depart the scope of the present disclosure.

FIG. 6 is a schematic diagram illustrating an exemplary tracking device 600 according to some embodiments of the present disclosure. In some embodiments, the tracking device 600 may be used as a component of the imaging apparatus 102 (e.g., the tracking device 420 or a part thereof). The tracking device 600 may include a shelter 610 and an X-ray receiver 620. The X-ray receiver 620 may be similar to the X-receiver 520 as illustrated in FIG. 5, and the description thereof is not repeated here.

The shelter 610 may have a shape of a cross. The shelter 610 may be formed by two elongated rods extending along different directions. The angle formed by the two elongated rods may be a value ranging from 0 to 180 degrees. For example, the angle formed by the two elongated rods may be 90 degrees. An elongated rod may be made of at least one highly absorbing material as described elsewhere in the disclosure. In some embodiments, the shelter 610 may also include an auxiliary structure to support or mount the two elongated rods (not shown in the figure). The auxiliary structure may be made of a poorly absorbing material as described elsewhere in the disclosure.

The shelter 610 and the X-ray receiver 620 may form an assembly that is situated before an X-ray source. When the shelter 610 and the X-ray receiver 620 are radiated by X-rays emitted from a focal spot of the X-ray source, the X-ray receiver 620 may receive attenuated X-rays that pass through the shelter 610 and unattenuated X-rays that are not attenuated by the shelter 610. The attenuated X-rays that pass through the shelter 610 may form a "shaded area" on the X-ray receiver 620, and the unattenuated X-rays that are not attenuated by the shelter 610 may form a "normal area" on the X-ray receiver 620. It shall be noted that the intensity of X-rays in a unit area of the "shaded area" may be less than the intensity of X-rays that strike a unit area in the "normal area." In some embodiments, the "shaded area" may have a shape of a cross that resembles the shape of the shelter 610.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the angle formed by the two elongated rods may be adjustable. However, those variations and modifications do not depart the scope of the present disclosure.

Figure 7:
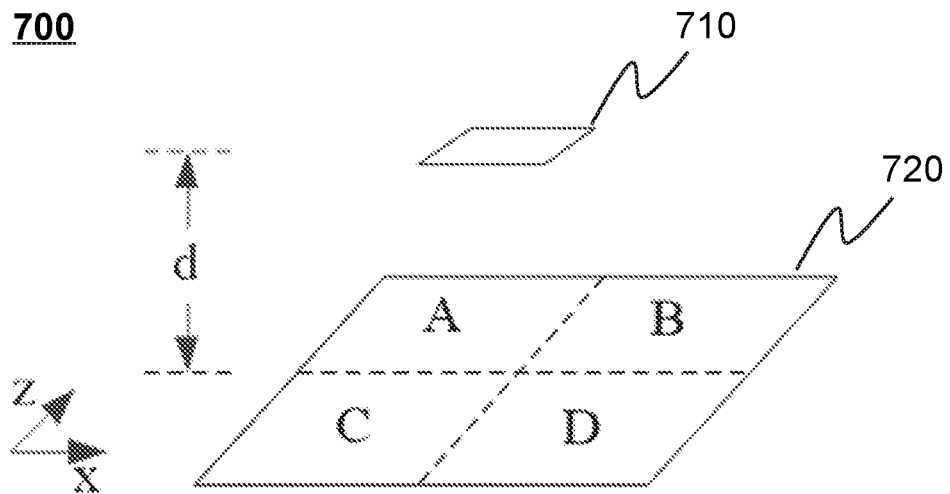
FIG. 7 is a schematic diagram illustrating an exemplary tracking device according to some embodiments of the present disclosure.

FIG. 7 is a schematic diagram illustrating an exemplary tracking device 700 according to some embodiments of the present disclosure. In some embodiments, the tracking device 700 may be used as a component of the imaging apparatus 102 (e.g., the tracking device 420 or a part thereof). The tracking device 700 may include a shelter 710 and an X-ray receiver 720. The shelter 710 may be similar to the shelter 510 as illustrated in FIG. 5, or the shelter 610 as illustrated in FIG. 6, and the description thereof is not repeated here.

The X-ray receiver 720 may include at least two X-ray receiving regions arranged in a first direction (e.g., the x-direction) and/or at least two X-ray receiving regions arranged in a second direction (e.g., the z-direction). For illustration purposes, the X-ray receiver 720 may be divided into a plurality of regions which includes a region A, a region B, a region C, and a region D. The region A may abut the region B in the first direction, and abut the region C in the second direction. The region D may abut the region B in the second direction and abut the region C in the first region. In some embodiments, the at least two X-ray receiving regions arranged in the first direction may include a first X-ray receiving region (e.g., formed by the region A and/or the region C) and a second X-ray receiving region (e.g., formed by the region B and/or the region D). The at least two X-ray receiving regions arranged in the second direction may include a third X-ray receiving region (e.g., formed by the region A and/or the region B) and a fourth X-ray receiving region (e.g., formed by the region C and/or the region D). In some embodiments, an X-ray receiving region arranged in the first direction (e.g., formed by the region A and the region C) may be overlapped or partially overlapped with an X-ray receiving region arranged in the second direction (e.g., formed by the region A and the region C).

When the shelter 710 and the X-ray receiver 720 are radiated by X-rays emitted from a focal spot of an X-ray source, an X-ray receiving region of the X-ray receiver 720 may receive at least a portion of attenuated X-rays that pass through the shelter 710 and at least a portion of unattenuated X-rays that are not attenuated by the shelter 710. The position of the focal spot of the X-ray source may be determined according to the different intensities of X-rays that strike different X-ray receiving regions of the X-ray receiver. For example, the position of the focal spot in the first direction may be determined according to the intensity of X-rays that strike the first X-ray receiving region and the intensity of X-rays that strike the second X-ray receiving region. As another example, the position of the focal spot in the second direction may be determined according to the intensity of X-rays that strike the third X-ray receiving region and the intensity of X-rays that strike the fourth X-ray receiving region. More description regarding the determination of the position of the focal spot may be found elsewhere in the disclosure (e.g., FIG. 10 and the description thereof).

The sizes of the plurality of X-ray receiving regions may be the same or different. For example, the sizes of the at least two X-ray receiving regions arranged in the first direction (e.g., the x-direction) may be the same or different. As another example, the sizes of the at least two X-ray receiving regions arranged in the second direction (e.g., the z-direction) may be the same or different. As still another example, the size of an X-ray receiving region arranged in the first direction (e.g., the x-direction) may be the same as or different from the size of an X-ray receiving region arranged in the second direction (e.g., the z-direction).

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, an X-ray receiving region may be composed of two or more separate regions of the X-ray receiver. Two separate regions of the X-ray receiver may be separated by a distance of one or more other regions. However, those variations and modifications do not depart the scope of the present disclosure.

Figure 8:
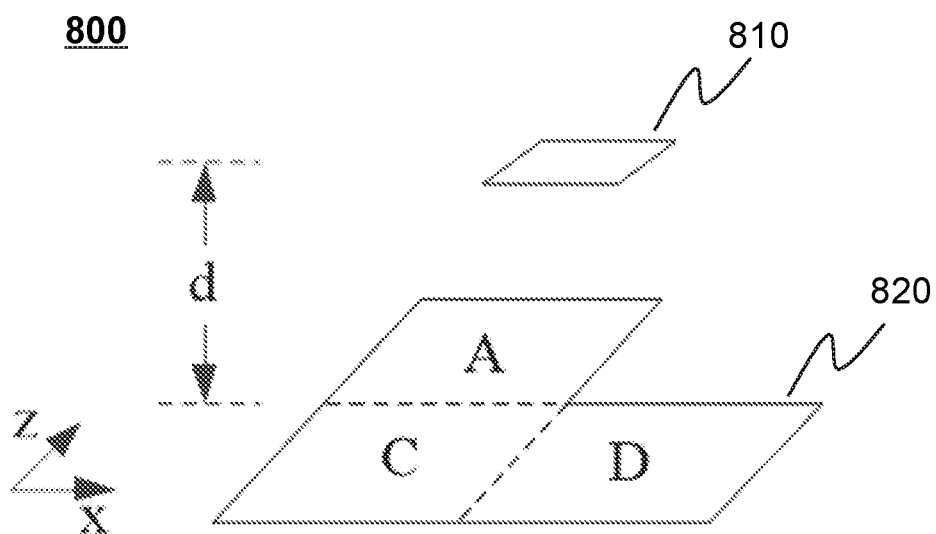
FIG. 8 is a schematic diagram illustrating an exemplary tracking device according to some embodiments of the present disclosure.

FIG. 8 is a schematic diagram illustrating an exemplary tracking device 800 according to some embodiments of the present disclosure. In some embodiments, the tracking device 800 may be used as a component of the imaging apparatus 102 (e.g., the tracking device 420 or a part thereof). The tracking device 800 may include a shelter 810 and an X-ray receiver 820. The shelter 810 may be similar to the shelter 510 as illustrated in FIG. 5, or the shelter 610 as illustrated in FIG. 6, and the description thereof is not repeated here.

The X-ray receiver 820 may include a region A, a region C, and a region D. In a first direction (e.g., the x-direction), the region C may form a first X-ray receiving region, and the region D may form a second X-ray receiving region. The position of the focal spot in the first direction may be determined according to the intensity of X-rays that strike the region C and the intensity of X-rays that strike the region D. Similarly, in a second direction (e.g., the z-direction), the region C may form a third X-ray receiving region, and the region A may form a fourth X-ray receiving region. Thus, the position of the focal spot in the second direction may be determined according to the intensity of X-rays that strike the region C and the intensity of X-rays that strike the region A.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the region A and the region C may be separated by a distance of one or more other regions. However, those variations and modifications do not depart the scope of the present disclosure.

Figure 9:
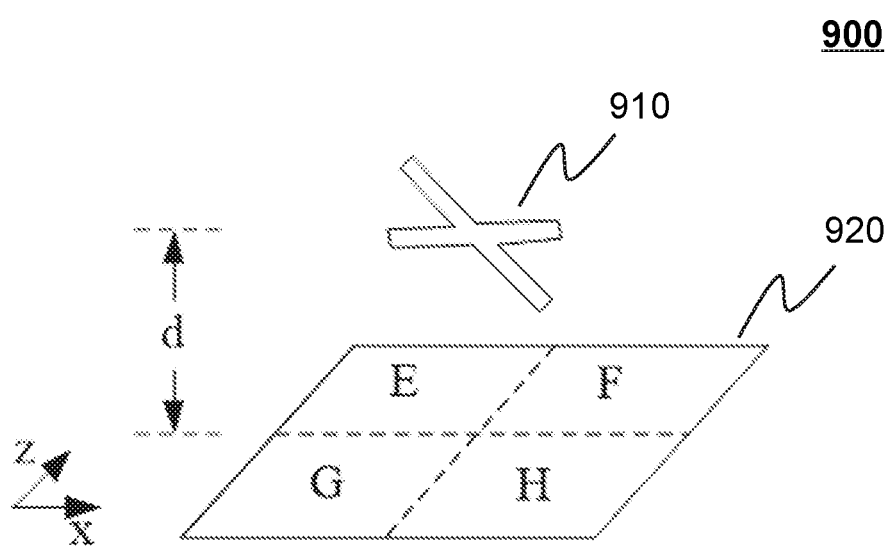
FIG. 9 is a schematic diagram illustrating an exemplary tracking device according to some embodiments of the present disclosure.

FIG. 9 is a schematic diagram illustrating an exemplary tracking device 900 according to some embodiments of the present disclosure. In some embodiments, the tracking device 900 may be used as a component of the imaging apparatus 102 (e.g., the tracking device 420 or a part thereof). The tracking device 900 may include a shelter 910 and an X-ray receiver 920. The shelter 910 may have a shape of a cross that is similar to the shelter the shelter 610 as illustrated in FIG. 6, and the description thereof is not repeated here. The X-ray receiver 920 may include a region E, a region F, a region F and a region G, which may be similar to the regions as illustrated in FIG. 7, and the description thereof is not repeated here.

Figure 10:
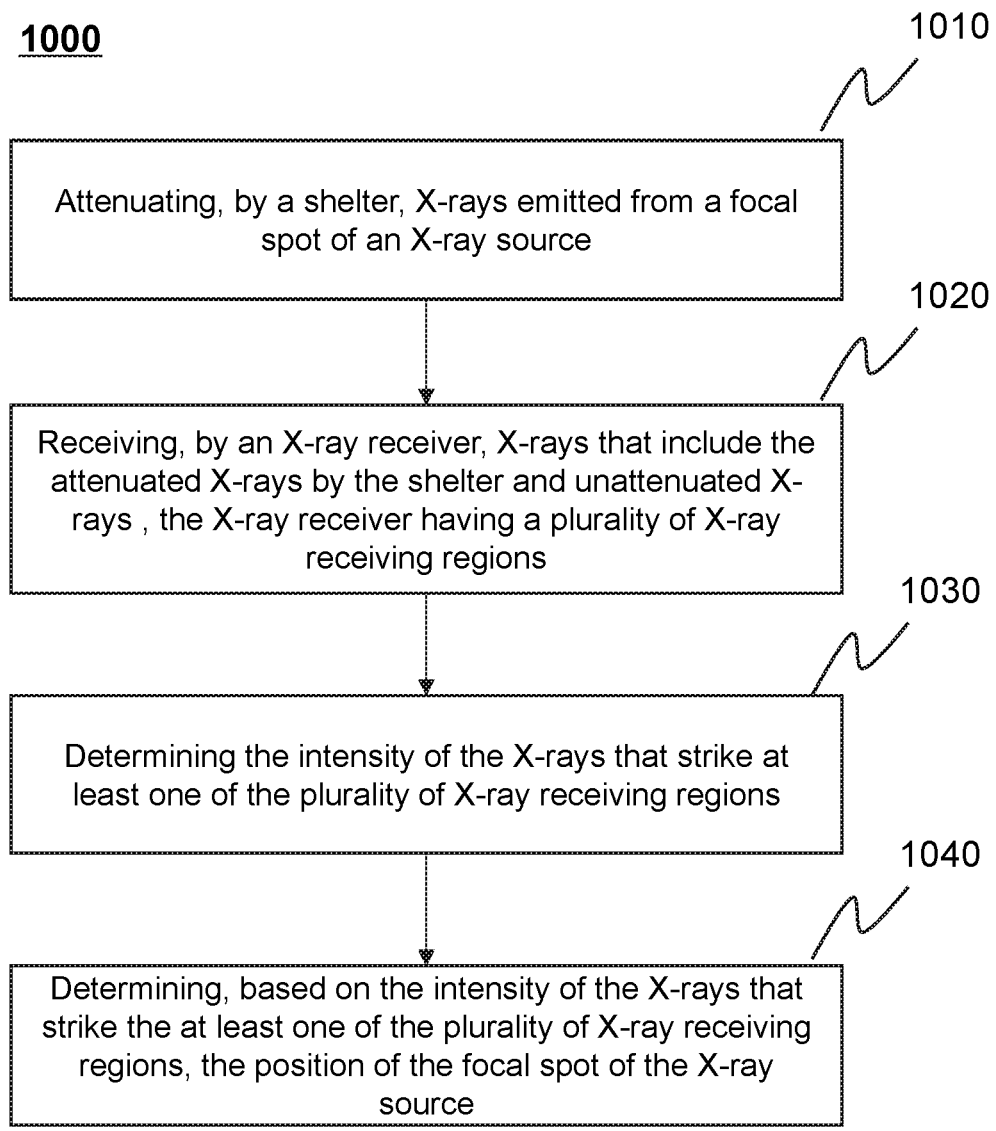
FIG. 10 is a flowchart of an exemplary process for determining a position of a focal spot of an X-ray source according to some embodiments of the present disclosure.

FIG. 10 is a flowchart illustrating an exemplary process for determining a position of a focal spot of an X-ray source according to some embodiments of the present disclosure. In some embodiments, at least a portion of the process 1000 may be executed on the tracking device 102. At least a portion of the process 1000 may be implemented in the computing device 200 illustrated in FIG. 2 (e.g., the processor 220) or the mobile device 300 illustrated in FIG. 3 (e.g., CPU 340).

In 1010, a shelter may attenuate X-rays emitted from a focal spot of an X-ray source (e.g., the X-ray source 410). The shelter may be the shelter 510 illustrated in FIG. 5, the shelter 610 illustrated in FIG. 6, the shelter 710 illustrated in FIG. 7, the shelter 810 illustrated in FIG. 8, or the shelter 910 illustrated in FIG. 9, and the description thereof is not repeated here.

In 1020, an X-ray receiver may receive X-rays, which may include the attenuated X-rays by the shelter and unattenuated X-rays from the focal spot of the X-ray source. The X-ray receiver may have a plurality of X-ray receiving regions. In some embodiments, an X-ray receiving region may receive at least a portion of the attenuated X-rays by the shelter and at least a portion of the unattenuated X-rays from the focal spot of the X-ray source.

In 1030, the intensity of the X-rays that strike at least one of the plurality of X-ray receiving regions may be determined by, for example, the tracking device 102 or the processing module 106. In some embodiments, the intensity of the X-rays that strike an X-ray receiving region arranged in a first direction may be determined. In some embodiments, the intensity of the X-rays that strike an X-ray receiving region arranged in a second direction may be determined.

For illustration purpose, the intensity of the X-rays that strike at least one of the plurality of X-ray receiving regions of the tracking device 700 illustrated in FIG. 7 is described as an example. For brevity, at time t, the intensity of X-rays that strike the region A may be expressed as $P_A(t)$, the intensity of X-rays that strike the region B may be expressed as $P_B(t)$, the intensity of X-rays that strike the region C may be expressed as $P_C(t)$, and the intensity of X-rays that strike the region D may be expressed as $P_D(t)$. The intensity of X-rays that strike a region may be in associated with an electrical signal generated by one or more detection units of the region. A first X-ray receiving region arranged in a first direction (e.g., the x-direction) may be formed by the region A and the region C, and thus the intensity of the X-rays that strike the first X-ray receiving region may be expressed as $P_A(t)+P_C(t)$. A second X-ray receiving region arranged in the first direction (e.g., the x-direction) may be formed by the region B and the region D, and thus the intensity of the X-rays that strike the second X-ray receiving region may be expressed as $P_B(t)+P_D(t)$. Similarly, a third X-ray receiving region arranged in a second direction (e.g., the z-direction) may be formed by the region A and the region B, and thus the intensity of the X-rays that strike the third X-ray receiving region may be expressed as $P_A(t)+P_B(t)$. A fourth X-ray receiving region arranged in the second direction (e.g., the z-direction) may be formed by the region C and the region D, and thus the intensity of the X-rays that strike the fourth X-ray receiving region may be expressed as $P_C(t)+P_D(t)$.

In 1040, the position of the focal spot of the X-ray source may be determined based on the intensity of the X-rays that strike the at least one of the plurality of X-ray receiving regions by, for example, the processing module 106. In some embodiments, the position of the focal spot may be determined according to a relationship between positions of the focal spot and distributions of intensities of the X-rays that strike the at least one of the plurality of X-ray receiving regions. The distribution of intensities of the X-rays that strike the at least one of the plurality of X-ray receiving regions may be expressed as various distribution related parameters.

For example, a first distribution related parameter may be expressed as the difference between the intensities of the X-rays that strike at least two of the plurality of X-ray receiving regions in a first direction (e.g., the x-direction). Referring to FIG. 7, the difference between the intensities of the X-rays that strike two X-ray receiving regions in the x-direction may be expressed as:

$$P_x(t)=(P_A(t)+P_C(t))-(P_B(t)+P_D(t)), \quad (1)$$

where $P_x(t)$ denotes the first distribution related parameter, $P_A(t)+P_C(t)$ denotes the intensity of the X-rays that strike the first X-ray receiving region in the x-direction, and $P_B(t)+P_D(t)$ denotes the intensity of the X-rays that strike the second X-ray receiving region in the x-direction.

As another example, a second distribution related parameter may be expressed as the difference between the intensities of the X-rays that strike at least two of the plurality of X-ray receiving regions in a second direction (e.g., the z-direction). Referring to FIG. 7, the difference between the intensities of the X-rays that strike two X-ray receiving regions in the z-direction may be expressed as:

$$P_z(t)=(P_A(t)+P_B(t))-(P_C(t)+P_D(t)), \quad (2)$$

where $P_z(t)$ denotes the second distribution related parameter, $P_A(t)+P_B(t)$ denotes the intensity of the X-rays that strike the third X-ray receiving region in the z-direction, and $P_C(t)+P_C(t)$ denotes the intensity of the X-rays that strike the fourth X-ray receiving region in the z-direction.

As still another example, a third distribution related parameter may be expressed as the ratio between the intensities of the X-rays that strike at least two of the plurality of X-ray receiving regions in a first direction (e.g., the x-direction). Referring to FIG. 7, the ratio between the intensities of the X-rays that strike two of the plurality of X-ray receiving regions in the x-direction may be expressed as:

$$P'_x(t)=(P_A(t)+P_C(t))/(P_B(t)+P_D(t)), \quad (3)$$

where $P'_x(t)$ denotes the third distribution related parameter.

As still another example, a fourth distribution related parameter may be expressed as the ratio between the intensities of the X-rays that strike at least two of the plurality of X-ray receiving regions in the second direction (e.g., the z-direction). Referring to FIG. 7, the ratio between the intensities of the X-rays that strike two of the plurality of X-ray receiving regions in the z-direction may be expressed as:

$$P'_z(t)=(P_A(t)+P_B(t))/(P_C(t)+P_D(t)), \quad (4)$$

where $P'_z(t)$ denotes the fourth distribution related parameter.

In some embodiments, the relationship between positions of the focal spot and distributions of intensities of the X-rays that strike the at least one of the plurality of X-ray receiving regions may be presented in the form of, for example, a lookup table, or a database. If a distribution of intensities of the X-rays that strike the at least one of the plurality of X-ray receiving regions (e.g., the value of a distribution related parameter) is determined, the corresponding position of the focal spot may be determined accordingly. For example, a value of the first distribution related parameter or the third distribution related parameter may correspond to a position of the focal spot in the first direction. A value of the second distribution related parameter or the fourth distribution related parameter may correspond to a position of the focal spot in the second direction. The relationship between positions of the focal spot and distributions of intensities of the X-rays that strike the at least one of the plurality of X-ray receiving regions may be stored in one or more storage (e.g., the storage module 112) in the form of, for example, data or instructions. In some embodiments, when a distribution of intensities of the X-rays that strike different X-ray receiving regions of a X-ray receiver is obtained by the processing module 106, the processing module 106 may retrieve the relationship between positions of the focal spot and distributions of intensities of the X-rays that strike the at least one of the plurality of X-ray receiving regions from a storage (e.g., the storage module 112), and further determine the position of the focal spot based according to the relationship.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the distribution of intensities of the X-rays that strike the at least one of the plurality of X-ray receiving regions may be expressed as other distribution related parameters. Specifically, the intensity of the X-rays that strike more than two X-ray receiving regions in the first/second direction may be used to define a distribution related parameter. However, those variations and modifications do not depart the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying a ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

What is claimed is:

1. A system for determining a position of a focal spot of an X-ray source, comprising:
   a tracking device radiated by the X-ray source, the tracking device including:
   a shelter configured to attenuate X-rays emitted from the focal spot of the X-ray source; and
   an X-ray receiver comprised of four X-ray receiving regions, each of the four X-ray receiving regions receiving X-rays that include attenuated X-rays by the shelter and unattenuated X-rays, wherein the shelter and the X-ray receiver are separated by a distance.

2. The system of claim 1, wherein the shelter and the X-ray receiver are configured to reside between the X-ray source and an X-ray detector for determining the position of the focal spot.

3. The system of claim 1, wherein the four X-ray receiving regions intersect at a geometric center of the X-ray receiver.

4. The system of claim 3, wherein the X-ray receiver is symmetrical with respect to the geometric center of the X-ray receiver.

5. The system of claim 1, further comprising:
   a storage device storing a set of instructions; and
   at least one processor in communication with the storage device, wherein when executing the instructions, the at least one processor is configured to cause the system to:
   determine an intensity of the X-rays that strike the four X-ray receiving regions; and
   determine, based on the determined intensity of the X-rays that strike the four X-ray receiving regions, the position of the focal spot of the X-ray source.

6. The system of claim 5, wherein to determine the intensity of the X-rays that strike the four X-ray receiving regions includes to:
   determine, for each of the four X-ray receiving regions, an intensity of the X-rays that strike the X-ray receiving region.

7. The system of claim 6, wherein to determine, based on the determined intensity of the X-rays that strike the four X-ray receiving regions, the position of the focal spot of the X-ray source includes to:
   determine, based on intensities of the X-rays that strike two X-ray receiving regions in a first direction, a position of the focal spot in the first direction,
   determine, based on intensities of the X-rays that strike two X-ray receiving regions in a second direction, a position of the focal spot in the second direction, the first direction being perpendicular to the second direction, and
   determine, based on the position of the focal spot in the first direction and the position of the focal spot in the second direction, the position of the focal spot.

8. The system of claim 7, wherein to determine the position of the focal spot in the first direction includes to:
   determine the position of the focal spot in the first direction based on a relationship between positions of the focal spot and distributions of intensities of the X-rays that strike the two X-ray receiving regions in the first direction.

9. The system of claim 7, wherein to determine the position of the focal spot in the first direction includes to:
   determine the position of the focal spot in the first direction based on a difference between the intensities of the X-rays that strike the two X-ray receiving regions arranged in the first direction.

10. The system of claim 7, wherein to determine the position of the focal spot in the first direction includes to:
    determine the position of the focal spot in the first direction based on a ratio between the intensities of the X-rays that strike the two X-ray receiving regions arranged in the first direction.

11. The system of claim 1, wherein the shelter has a shape of a cross, a rectangle, a circle, or a triangle.

12. A method for determining a position of a focal spot of an X-ray source, comprising:
    attenuating, by a shelter, X-rays emitted from the focal spot of the X-ray source,
    receiving, by each of four X-ray receiving regions composing an X-ray receiver, X-rays that include the attenuated X-rays by the shelter and unattenuated X-rays;
    determining, by at least a processor, an intensity of the X-rays that strike each of the X-ray receiving regions; and
    determining, based on the intensities of the X-rays that strike the four X-ray receiving regions, the position of the focal spot of the X-ray source.

13. The method of claim 12, wherein the shelter and the X-ray receiver are configured to reside between the X-ray source and an X-ray detector for determining the position of the focal spot.

14. The method of claim 12, wherein the shelter has a shape of a cross, a rectangle, a circle, or a triangle.

15. The system of claim 12, wherein the four X-ray receiving regions intersect at a geometric center of the X-ray receiver.

16. The system of claim 15, wherein the X-ray receiver is geometric symmetrical with respect to the geometric center of the X-ray receiver.

17. The method of claim 12, wherein
    determining, based on the intensities of the X-rays that strike the four X-ray receiving regions, the position of the focal spot of the X-ray source includes:
    determining, based on intensities of the X-rays that strike two X-ray receiving regions in a first direction, a position of the focal spot in the first direction,
    determining, based on intensities of the X-rays that strike two X-ray receiving regions in a second direction, a position of the focal spot in the second direction, and
    determining, based on the position of the focal spot in the first direction and the position of the focal spot in the second direction, the position of the focal spot.

18. The method of claim 17, wherein determining the position of the focal spot in the first direction includes:
    determining the position of the focal spot in the first direction based on a relationship between positions of the focal spot and distributions of intensities of the X-rays that strike the two X-ray receiving regions in the first direction.

19. The method of claim 17, wherein determining the position of the focal spot in the first direction includes:
    determining the position of the focal spot in the first direction based on a difference between the intensities of the X-rays that strike the two X-ray receiving regions in the first direction.

20. The method of claim 17, wherein determining the position of the focal spot in the first direction includes:

determining the position of the focal spot in the first direction based on a ratio between the intensities of the X-rays that strike the two X-ray receiving regions in the first direction.

* * * * *